United States Patent
Roh et al.

(10) Patent No.: US 6,417,403 B1
(45) Date of Patent: Jul. 9, 2002

(54) PROCESS FOR PREPARING CHIRAL (S)-2,3-DISUBSTITUTED-1-PROPYLAMINE DERIVATIVES

(75) Inventors: Kyoung Rok Roh; Jung Hwan Lee, both of Daejeon; Dae Il Hwang, Incheon; Won Jang Lee; Kyung-Il Kim, both of Daejeon, all of (KR)

(73) Assignee: Samsung Fine Chemicals Co., Ltd., Ulsan (KR)

(*) Notice: Subject to any disclaimer, the term of this patent is extended or adjusted under 35 U.S.C. 154(b) by 0 days.

(21) Appl. No.: 09/673,123

(22) PCT Filed: Apr. 14, 1999

(86) PCT No.: PCT/KR99/00178

§ 371 (c)(1),
(2), (4) Date: Dec. 7, 2000

(87) PCT Pub. No.: WO99/52855

PCT Pub. Date: Oct. 21, 1999

(30) Foreign Application Priority Data

Apr. 14, 1998 (KR) .............................................. 98-13172
Apr. 14, 1998 (KR) .............................................. 98-13173
Apr. 14, 1998 (KR) .............................................. 98-13174

(51) Int. Cl.[7] .............................................. C07C 209/50
(52) U.S. Cl. ........................ 564/468; 564/486; 564/488
(58) Field of Search .............................. 564/468, 486, 564/488

(56) References Cited

U.S. PATENT DOCUMENTS

| | | | |
|---|---|---|---|
| 3,855,283 A | 12/1974 | Cohen et al. | |
| 4,900,847 A | 2/1990 | Hanson et al. | |
| 5,292,939 A | 3/1994 | Hollingsworth | |
| 5,319,110 A | 6/1994 | Hollingsworth | |
| 5,374,773 A | 12/1994 | Hollingsworth | |

FOREIGN PATENT DOCUMENTS

| | | |
|---|---|---|
| EP | 628536 A2 | 12/1994 |
| WO | WO 83/01770 | 5/1983 |
| WO | WO 91/10642 | 7/1991 |

OTHER PUBLICATIONS

Pine, Hendrickson, Cram and Hammond, Organic Chemistry 4 ed., McGraw–Hill Inc., NY, 1980, pp. 906–908.*
Tetrahedron Letters, vol. 27, No. 18, pp. 2061–2062, 1986.
Argic. Biol. Chem., 48, 2055 (1984).
Agric. Biol. Chem., 49, 1669 (1985).
Agric. Biol. chem., 46, 1593 (1982).

* cited by examiner

Primary Examiner—Brian J. Davis
(74) Attorney, Agent, or Firm—Finnegan, Henderson, Farabow, Garrett & Dunner LLP

(57) ABSTRACT

A process for the preparation of chiral (S)-2,3-disubstituted-1-propylamine derivatives, in which a carbonyl group of (S) 3,4-disubstituted-1-butanecarbonyl derivatives is converted to an amine group, and the conversion reaction is performed through Curtius rearrangement or Hoffman rearrangement.

21 Claims, No Drawings

PROCESS FOR PREPARING CHIRAL (S)-2,3-DISUBSTITUTED-1-PROPYLAMINE DERIVATIVES

This application is 371 of PCT/KR99/00178 filed Apr. 14, 1999.

BACKGROUND OF THE INVENTION

1. Field of the Invention

The present invention relates to a process for preparing chiral (S)-2,3-disubstituted-1-propylamine derivatives and more particularly, to the process for preparing chiral (S)-2,3-disubstituted-1-propylamine derivatives expressed in the following formula 1, performed in such a manner that a carbonyl group of chiral (S)-3,4-disubstituted-1-butanecarbonyl derivatives expressed in the following formula 2 is converted to an amine group through decarbonylation without influence on chirality, whereby preparing amine compound whose carbon backbone number is decreased bad one:

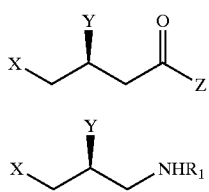

wherein,
- $R_1$ represents hydrochloric acid salt (H.HCl), sulfuric acid salt (H.H$_2$SO$_4$) or —C(O)OR$_2$;
- $R_2$ represents linear or branched alkyl chain having carbon atoms of 1–10, benzyl or phenyl group;
- X and Y which are same or different, represents a halogen atom, hydroxy group, acetate group, sulfonate group, or in which X and Y are combined to form epoxy group, acetonide group; and
- Z represents NH$_2$, NHNH$_2$ or hydroxy group.

2. Description of the Related Art

A chiral (S)-2,3-disubstituted-1-propylamine derivatives expressed in the formula 1 has been well known as key intermediates for preparing β-blocker used as antihypertensive drug. β-Blocker drugs employing (S)-3-amino-1,2-propanediol or salt thereof as raw material include (S)-atenolol, (S)-metoprolol, (S)-nadolol, (S)-timolol. A numerous study has been conducted on a process for synthesizing a compound expressed in the formula 2 or derivatives thereof as follows:

In the case of a compound having 3 carbon atoms in backbone and chiral hydroxy group at C-2, an introduction of oxygen functional group with chirality to C-2 position may be achieved from a racemic compound having 3 carbon atoms in backbone by biologically selective hydrolysis employing microorganism or enzyme.

*Tetrahedron Lett.* 27, 2061(1992) discloses the process for preparing chiral 1-amino-2-propanol derivatives through selective hydrolysis of racemic 2-hydroxy-1-propylamide protected by N-phenylacetyl using benzylpenicillinacylase. However, the theoretical yield of hydrolysis using the above enzyme is no more than 50%; thus optical purity is extremely low as optical isomeric ratio is 65:35.

*Agric. Biol. Chem.,* 48, 2055(1984) and *Agric. Biol. Chem.,* 49, 1669(1985) discloses a process for preparing (S)-ester through selective hydrolysis of racemic 2-oxazolidoneester using lipase; however, the yield thereof is 35%, that is to say, very low; and additional 5 steps are required to convert prepared (R)-alcohol to desired (S)-alcohol.

A process for preparing chiral (S)-2,3-dichloro-1-propylacetate through selective hydrolysis of racemic 2,3-dichloro-1-propylacetate using lipase is described in *Agric. Biol. Chem.,* 46, 1593(1982); however, the yield thereof is 9–25% which is too low to be commercialized; and on top of that, 4 steps are required to manufacture racemic 2,3-dichloro-1-propylacetate from propene.

U.S. Pat. No. 4,900,847(1990) discloses a process for preparing chiral (S)-2,3-epoxypropanol through catalytic asymmetric epoxidation of allylic alcohol. The process shows higher yield than the above-described, biological selective hydrolysis, while it shows low optical isomeric efficiency, 89%ee. The conventional methods as described above exhibit yield no more than 50%, performed in such a way that racemic compound having 3 carbon atoms in backbone is prepared and then chiral hydroxy group is introduced into it so as to prepare optical active intermediates having 3 carbon atoms in backbone.

SUMMARY OF THE INVENTION

Accordingly, an object of this invention is to provide a novel process for the preparation of chiral (S)-2,3-disubstituted-1-propylamine derivatives using chiral (S)-3,4-disubstituted-1-butanecarbonyl derivatives with high purity as starting material that may be economically obtained from natural product, whereby decreasing the production cost and solving the problems of the conventional methods, i.e. lower optical purity and yield, performed in such a way that chiral center is introduced.

DETAILED DESCRIPTION OF THE INVENTION

This invention is characterized by a process for preparing chiral (S)-2,3-disubstituted-1-propylamine derivatives expressed in the following formula 1, in which a carbonyl group of chiral (S)-3,4-disubstituted-1-butanecarbonyl derivatives expressed in the following formula 2 is converted to an amine group:

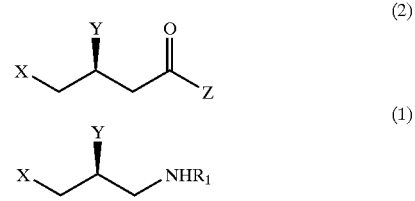

wherein,
- $R_1$ represents hydrochloric acid salt (H.HCl), sulfuric acid salt (H.H$_2$SO$_4$) or —C(O)OR$_2$;
- $R_2$ represents linear or branched alkyl chain having carbon atoms of 1–10, benzyl or phenyl group;
- X and Y which are same or different, represents a halogen atom, hydroxy group, acetate group, sulfonate group, or in which X and Y are combined to form epoxy group, acetonide; and
- Z represents NH$_2$, NHNH$_2$ or hydroxy group.

This invention is explained in more detail as follows:
This invention relates to a process for preparing amine compound whose carbon backbone number is decreased by one, performed in such a manner that a carbonyl group is converted to an amine group without influence on chirality of starting material. The principle mechanism of this invention is explained by Curtius Rearrangement or Hofmann Rearrangement. As reported thus far; there have not been preparative examples that propyl amine derivatives with chiral oxygen substituents at C-2 are prepared simultaneously with decreasing of carbon backbone number from 4 to 3 by Curtius Rearrangement or Hofmann Rearrangement.

This fact may be described as follows:

The following scheme 1 shows a preparing example of a compound of formula 1 through Hofmann Rearrangement using a compound of formula 2 (where, Z is $NH_2$).

Scheme 1

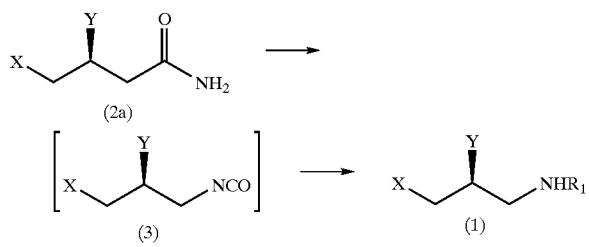

wherein, X, Y and $R_1$ are the same as the above-specified.

According to the scheme 1, a chiral (S)-3,4-disubstituted-1-butylamide represented in formula 2a is oxidized to induce Hofmann Rearrangement, which generates isocyanate intermediate and then converted to amino group, finally producing a compound of this invention. If the final product whose $R_1$ is inorganic acid salt (eg., hydrochloric acid salt (H.HCl), sulfuric acid salt ($H.H_2SO_4$)) is desired, hydrochloric acid or sulfuric acid should be added to a reaction mixture containing an intermediate represented in formula 3; if the final product whose $R_1$ is carbamate is desired, alcohols should be added to.

According to this invention, it is preferred that the Hofmann Rearrangement is performed in the presence of alkaline metal hydroxide and halogen, or MOX (where, M is alkaline metal atom and X is halogen atom) which is generated in reaction of alkaline metal hydroxide and halogen, such as sodium hypochlorite, sodium hypobromite and potassium hypochlorite.

In the Hofmann Rearrangement, it is preferred that water or polar organic solvent is employed as solvent; more preferably, $C_1$-$C_{10}$ alcohol. The reaction temperature is preferably in the range of 0–100° C.; more preferably 0–60° C. If the temperature is lower than 0° C., the reaction is scarcely proceeded; but in case of exceeding 100° C., the racemization on chiral center is occurred.

The chiral (S)-3,4-disubstituted-1-butylamide used as starting material in scheme 1 is prepared with optical purity of at least 99%ee by very inexpensive and simple method (Japanese Unexamined Publication No. Sho64-13069), from (S)-3-hydroxybutyrolactone obtained through known method (U.S. Pat. Nos. 5,374,773; 5,319,110; and 5,292,939).

The following scheme 2 represents a preparing example of a compound of formula 1 through Curtius Rearrangement using a compound of formula 2 (where, Z is $NHNH_2$).

Scheme 2

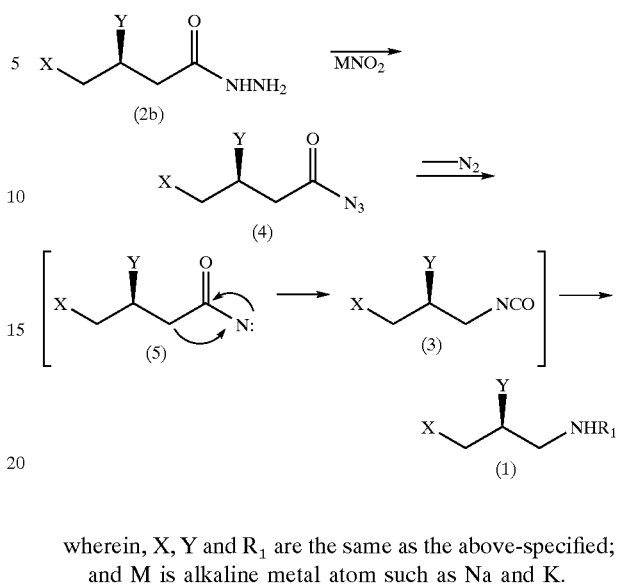

wherein, X, Y and $R_1$ are the same as the above-specified; and M is alkaline metal atom such as Na and K.

As shown in the scheme 2, (S)-3,4-disubstituted-1-butylhydrazide represented in formula 2b is reacted with metallic nitrite or alkylnitrite to convert hydrazide group to acylazide group and then is subjected to reflux under reaction solvent, thereby releasing nitrogen gas, finally converting acylnitrene group of intermediate represented in formula 5 to isocyanate group.

In the above reaction, the step of conversion of hydrazide group of the compound represented in formula 2b to acylazide group is conducted preferably at temperature of −78–50° C.; if the temperature is less than −78° C., the reaction is scarcely proceeded; but in case of exceeding 50° C., the acylazide is decomposed. Preferably, alkaline metallic nitrite such as sodium nitrite and potassium nitrite is employed as metallic nitrite. It is preferred that alkylnitrite of $C_1$-$C_{10}$ is employed as alkylnitrite; more preferably, alkylnitrite of $C_1$-$C_6$.

As a solvent for reflux so as to convert the compound represented in formula 4 to the compound represented in formula 3, aromatic hydrocarbon such as benzene and toluene is preferred.

If an inorganic acid such as hydrochloric acid or sulfuric acid is added to a reaction mixture containing intermediate represented in formula 3, the final product whose $R_1$ is inorganic acid salt (eg., hydrochloric acid salt (H.HCl), sulfuric acid salt ($H.H_2SO_4$)) is obtained. If alcohols in place of inorganic acid is added, the final product whose $R_1$ is carbamate is provided.

The following scheme 3 represents a preparing example of a compound of formula 1 through Curtius Rearrangement using a compound of formula 2 (where, Z is OH).

Scheme 3

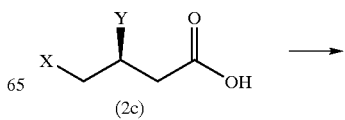

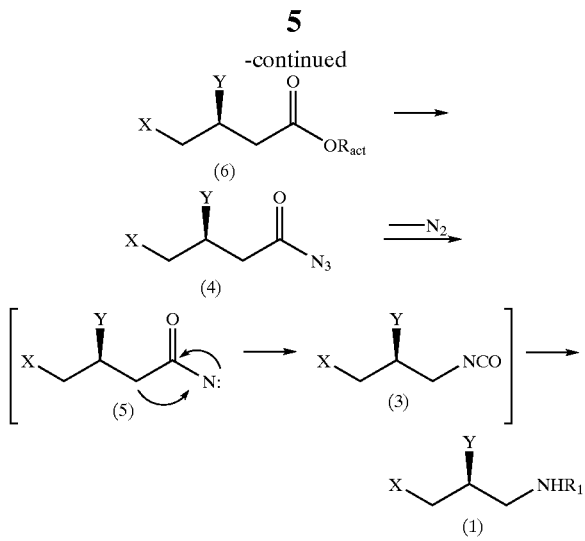

wherein, X, Y and $R_1$ are the same as the above-specified; and $R_{act}$ is carboxylic acid ester or phosphoric acid ester.

As shown in the scheme 3, carboxyl group of (S)-3,4-disubstituted-1-butyric acid represented in formula 2c is converted to activated ester group (eg., carboxylic acid ester or phosphoric acid ester) and then is subjected to nucleophilic substitution by using alkaline metal azide (eg., sodium azide, potassium azide), thereby preparing acylazide intermediate expressed in formula 4. Thereafter, the acylazide intermediate is subjected to reflux in the presence of suitable solvent, thereby releasing nitrogen gas and finally acylnitrene group of intermediate represented in formula 5 is converted to isocyanate group by Curtius Rearrangement. In the above reaction, the step of conversion of carboxyl group of the compound represented in formula 2c to acylazide group is conducted preferably at temperature of −78–50° C.; if the temperature is less than −78° C., the reaction is scarcely proceeded; but in case of exceeding 50° C., the acylazide is decomposed. As a solvent for reaction, aromatic hydrocarbon such as benzene and toluene is preferred. In the step of conversion of the above carboxyl group to activated ester group, the haloformate expressed in the following formula 7 or the phosphoryl halide expressed in the following formula 8 is added as reacting material:

$$X-\overset{O}{\underset{\|}{C}}-OR \quad (7)$$

$$X-\overset{O}{\underset{\|}{P}}-(OR)_2 \quad (8)$$

wherein,
X is a halogen atom; and
R is alkyl group of $C_1$–$C_5$, benzyl or phenyl group.

If an inorganic acid such as hydrochloric acid or sulfuric acid is added to a reaction mixture containing isocyanate intermediate represented in formula 3, the final product whose $R_1$ is inorganic acid salt (eg., hydrochloric acid salt (H.HCl), sulfuric acid salt ($H.H_2SO_4$)) is obtained. If alcohols in place of inorganic acid is added, the final product whose $R_1$ is carbamate is provided.

A solvent for extraction of acylazide in aqueous solution includes organic solvent which is immiscible with water such as chloroform, dichloromethane, diethylether, diisopropylether, dipropylether, benzene and tolune.

The following specific examples are intended to be illustrative of the invention and should not be construed as limiting the scope of the invention as defined by appended claims.

PREPARATIVE EXAMPLE 1

Preparation of (S)-3,4-Dihydroxy-1-butylhydrazide

Chiral (S)-3-hydroxybutyrolactone (16.32 g, 0.16 mol), hydrazine monohydrate (purity 80% 20 g, 0.32 mol) and ethanol (200 ml) in 500 ml flask equipped with thermometer and reflux condenser were stirred for 2 hours under reflux. The reaction mixture was cooled down to room temperature and stirred for additional 2 hours A white precipitate was filtered and dried to yield (S)-3,4-dihydroxy-1-butylhydrazide (95%, optical purity>99%ee).

$^1$H-NMR($D_2O$, ppm): δ3.92 (m, 1H, —CHOH), 3.32–3.47 (m, 2H, $CH_2OH$), 2.12–2.30 (m, 2H, $CH_2$—CO)

PREPARATIVE EXAMPLE 2

(S)-3-Acetoxy-4-bromo-1-butylhydrazide Hydrobromic Acid Salt

To 30% hydrobromic acid/acetic acid (62 ml, 0.23 mol) in 100 ml flask equipped with thermometer was added (S)-3,4-dihydroxy-1-butylhydrazide (13.4 g, 0.1 mol). The reaction mixture was stirred for 1 hour at ambient temperature. The precipitate was filtered, washed with 50 ml diethyl ether and dried to give (S)-3-acetoxy-4-bromo-1-butylhydrazide hydrobromic acid salt (93%, optical purity>99%).

$^1$H-NMR($D_2O$, ppm): δ5.34(m, 1H, —CHOAc), 3.50(m, 2H, $CH_2Br$), 2.75 (m, 2H, $CH_2$—CO), 2.06 (s, $OCOCH_3$)

EXAMPLE 1

(S)-3-Bromo-2-hydroxy-1-propylamine Hydrochloric Acid Salt (S)-3-Acetoxy-4-bromo-1-butylhydrazide hydrobromic acid salt (21.8 g, 0.092 mol), distilled water (80 ml), concentrated hydrochloric acid (40 ml) and diethyl ether (100 ml) in 250 ml flask equipped with thermometer were stirred at 0° C. To the reaction mixture was dropped a solution of sodium nitrite(16 g, 0.23 mol) in water (30 ml) while keeping temperature at lower than 10° C. After dropping, the reaction was extracted twice with diethyl ether (100 ml). The combined organic layer was dried over anhydrous $MgSO_4$ and filtered. The filtrate was evaporated. Toluene (50 ml) was added to the residue and refluxed for 15 min. to generate $N_2$ gas and then concentrated hydrochloric acid (40 ml) was added and refluxed for another 30 min. to generate $CO_2$. The reaction mixture was cooled down and evaporated to give white (S)-3-bromo-2-hydroxy-1-propyl amine hydrochloric acid salt (93%, optical purity>99%,)

$^1$H-NMR ($D_2O$, ppm) : δ4.03 (m, 1H, —CHOH), 3.41 (m, 2H, $CH_2Br$), 3.17 (d, 1H, $CH_aN$), 2.96 (t, 1H, $CH_bN$)

EXAMPLE 2

Preparation of (S)-3-Bromo-2-hydroxy-1-propylcarbamate Benzyl Ester (S)-3-Acetoxy-4-bromo-1-butylhydrazide hydrobromic acid salt (21.8 g, 0.092 mol), distilled water (80 ml), concentrated hydrochloric acid (40 ml) and stirred at 0° C. To the reaction mixture was dropped sodium nitrite (16 g, 0.23 mol) in water (30 ml) while keeping temperature at lower than 10° C. After dropping, the reaction mixture was extracted twice with diethyl ether (100 ml). The combined organic layer was dried over anhydrous $MgSO_4$ and filtered. The filtrate was evaporated. Toluene (50 ml) and benzyl alcohol (9.9 g, 0.092 mol) were added to the residue and then the reaction mixture was refluxed for 2 hours. The reaction mixture was evaporated to give white (S)-3-bromo-2-hydroxy-1-propylcarbamate benzyl ester (94%, optical purity>99%).

$^1$H-NMR ($CDCl_3$, ppm): δ7.39 (s, 5H, Ph), 5.52 (brs, 1H, NH), 5.28 (s, 2H, $CH_2$—Ph), 4.02 (m, 1H, CH—O), 3.48 (m, 2H, $CH_2$—Br), 3.36 (m, 2H, $CH_2N$)

EXAMPLE 3

Preparation of (S)-3-Chloro-2-Hydroxy-1-Propyl Amine Hydrochloric Acid Salt (S)4-Chloro-3-hydroxy-1-butylhydrazide (18 g, 0.119 mol) in 250 ml three-necked flask equipped with thermometer was dissolved in a mixture of 6 g hydrochloric acid in ethanol. Amyl nitrite (19.3 g, 0.165 mol) was added and the reaction mixture was heated to 60° C. for 2 hours. After cooling down the reaction mixture, diethyl ether (100 ml) was added and stirred. To the pricipitate filtered was added concentrated hydrochloric acid (200 ml). The reaction mixture was stirred for 2 hours at 90° C. It was cooled down in the ice bath and triturated with diethyl ether (300 ml) to give (S)-3-chloro-2-hydroxy-1-propylamine hydrochloric acid salt (91%, optical purity>99%ee).

$^1$H-NMR ($D_2O$, ppm): δ4.12 (m, 1H, —CHOH), 3.42–3.62 (m, 2H, $CH_2Cl$), 3.20 (d, 1H, $CH_aN$), 3.02 (t, 1H, $CH_bN$)

EXAMPLE 4

Preparation of (S)-2,3-Dihydroxy-1-propyl Amine Sulfuric Acid Salt (S)-3,4-Dihydroxy-1-butylhydrazide (13.4 g, 0.1 mol), distilled water (80 ml), concentrated sulfuric acid (30 ml) and diethyl ether (100 ml) in 250 ml flask equipped with thermometer were stirred at 0° C. To the reaction mixture was dropped a solution of sodium nitrite (16 g, 0.23 mol) in distilled water (30 ml) while keeping the temperature at lower than 10° C. After dropping, the reaction mixture was extracted twice with diethyl ether (150 ml). The combined organic layer was dried over anhydrous $MgSO_4$ and filtered. The filtrate was evaporated. Toluene (50 ml) was added to the residue and refluxed for 15 min. to generate $N_2$ gas. Concentrated sulfuric acid (30 ml) was added to the reaction mixture and refluxed for 1 hour to generate $CO_2$. The reaction mixture was then cooled and evaporated to give white (S)-2,3-dihydroxy-1-propylamine sulfuric acid salt (93%, optical purity>99%ee).

$^1$H-NMR ($D_2O$, ppm): δ3.92 (m, 1H, —CHOH), 3.53 (m, 2H, $CH_2OH$), 3.15–2.93 (m, 2H, $CH_2N$)

EXAMPLE 5

Preparation of (S)-3,4-O-Isopropyl iden-3,4-Dihydroxy-1-Butyric Acid Methyl Ester (S)-3-Hydroxyburyrolactone (102 g, 1 mol), 2,2-dimethoxypropane (200 ml), acetone (100 ml), methanol (20 ml) and p-toluenesulfonic acid monohydrate (10 g, 0.053 mol) in 1l flask equipped with thermometer and reflux condenser were refluxed for 3 hours. The reaction mixture was dissolved in diethyl ether (500 ml) and washed with a saturated solution of $NaHCO_3$ (100 ml). The organic solution was dried over anhydrous $MgSO_4$ and evaporated under the vacuum to give (S)-3,4-O-isopropyl iden-3,4-dihydroxy-1-butyric acid methyl ester (92%, optical purity>99%ee).

$^1$H-NMR ($CDCl_3$, ppm): δ4.41 (m, 1H, —CHO), 4.08 (m, 1H, $CH_{2a}O$), 3.63 (s, 3H, $OCH_3$), 3.58 (m, 1H, $CH_{2b}O$), 2.42–2.68 (m, 2H, $CH_2CO$), 1.34 (s, 3H, $OCH_3$)

EXAMPLE 6

Preparation of (S)-3,4-O-Isopropyl iden-3,4-Dihydroxy-1-Butyric Acid (S)-3,4-O-Isopropyliden-3,4-dihydroxy-1-butyric acid methyl ester (37.1 g, 0.0213 mol) in 500 ml three-necked flask equipped with thermometer was dissolved in THF (30 ml) and water (140 ml). Lithium hydroxide (2.2 g, 0.064 mol) was dropped at ambient temperature and stirred for 12 hours. 10% Aqueous solution of citric acid was added to adjust pH 4. The reaction mixture was extracted three times with diethyl ether (150 ml). The combined organic layer was dried over anhydrous $MgSO_4$ and evaporated to give (S)-3,4-O-isopropyliden-3,4-dihydroxy-1-butyric acid (92%, optical purity>99%ee).

$^1$H-NMR ($CDCl_3$, ppm): δ4.47 (m, 1H, CHO), 4.19 (m, 1H, —$CH_2O$), 3.69 (m, 1H, $CH_2O$), 2.80–2.17 (m, 2H, $CH_2O$), 1.44 (s, 3H, $OCH_3$), 1.37 (s, 3H, $OCH_3$)

EXAMPLE 7

Preparation of (S)-2,3-O-Isopropyliden-2,3-Dihydroxy-1-Propylcarbamate Benzyl Ester (S)-3,4-O-Isopropyliden-3,4-dihydroxy-1-butyric acid (3.2 g, 0.02 mol) in 500 ml three-necked flask was dissolved in acetone (100 ml) and cooled down to −10° C. Triethylamine (2.22 g, 0.022 mol) was added by keeping temperature at −10° C. and stirred for 20 min. Ethylchloroformate (2.39 g, 0.022 mol) was added and stirred for 30 min. by keeping temperature at 0° C. Sodium azide (2.6 g, 0.04 mol) dissolved in water (30 ml) was added and stirred for additional 30 min. by keeping temperature at 0° C. The reaction mixture was extracted three times with diethyl ether (100 ml). The combined organic layer was dried over anhydrous $MgSO_4$ and evaporated to dryness. Toluene (20 ml) was added to the residue. Benzyl alcohol (2.16 g, 0.02 mol) was added and refluxed for 1 hour. The reaction mixture was evaporated and purified by column chromatograpy on silica gel to give (S)-2,3-O-isopropyliden-2,3-dihydroxy-1-propylcarbamate benzyl ester (93%, optical purity>99%ee).

$^1$H-NMR ($CDCl_3$, ppm): δ7.29 (s, 5H, Ph), 5.61 (brs, 1H, NH), 5.05 (s, 2H, $CH_2Ph$), 4.12 (m, 1H, CH—O), 3.94 (m, 1H, $CH_{2a}$—O), 3.59 (m, 1H, $CH_{2b}$—O), 3.14–3.40 (m, 2H, $CH_2N$), 1.37 (s, 3H,$OCH_3$), 1.29 (s, 3H, $OCH_3$)

EXAMPLE 8

Preparation of (S)-2,3-O-Isopropyliden-2,3-Dihydroxy-1-Propylcarbamate t-Butyl Ester (S)-3,4-O-Isopropyliden-3,4-dihydroxy-1-butyric acid (3.2 g, 0.02 mol) in 500 ml three-necked flask was dissolved in acetone (230 ml) and stirred. Diphenylphosphorylazide (5.1 ml, 0.024 mol) and triethylamine (3.24 ml, 0.024 mol) were added and heated to reflux for 2 hours. 2-Methyl-2-propanol (3.24 ml, 0.04 mol) was added and refluxed for additional 12 hours. The reaction mixture was evaporated and dissolved in water. The reaction mixture was extracted three times with ethyl acetate (50 ml). The organic layer was washed with sat. aqueous solution of NaHCO$_3$ and dried over anhydrous MgSO$_4$. The organic layer was evaporated to dryness and purified by column chromatography on silica gel to give (S)-2,3-O-isopropyliden-2,3-dihydroxy-1-propylcarbamate t-butylester. (91%, optical purity>99%ee).

$^1$H-NMR (CDCl$_3$, ppm): δ5.54 (brs, 1H, NH), 4.22 (m, 1H, CH—O), 4.05 (m, 1H, CH$_{2a}$—O), 3.64 (m, 1H, CH$_{2b}$—O), 3.24–3.48 (m, 2H, CH$_2$N), 1.43 (s, 9H, O(CH$_3$)$_3$), 1.33 (s, 6H, 2OCH$_3$)

EXAMPLE 9

Preparation of (S)-2,3-Dihydroxy-1Propylcarbamate Benzyl Ester (S)-2,3-O-Isopropyliden-2,3-dihydroxy-1-propylcarbamate benzyl ester (2.51 g, 0.01 mol) in 100 ml flask was dissolved in acetonitrile (30 ml). 1N hydrochloric acid was added and stirred for 12 hours. The reaction mixture was extracted three times with ethyl acetate (50 ml). The combined organic layer was dried over anhydrous MgSO$_4$ and evaporated to give (S)-2,3-dihydroxy-1-propylcarbamate benzyl ester (90%, optical purity>99%ee).

$^1$H-NMR (CDCl$_3$, ppm) : δ7.37 (s, 5H, Ph), 5.13 (s, 2H, CH$_2$—Ph), 3.91 (m, 1H, CH—O), 3.62 (m, 2H, CH$_2$—O), 3.36 (m, 2H, CH$_2$N)

EXAMPLE 10

Preparation of (S)-2,3-Epoxy-1-Propylcarbamate Benzyl Ester (S)-2,3-Dihydroxy-1-propylcarbamate benzyl ester (2.11 g, 0.01 mol) in 100 ml flask was dissolved in CHCl$_3$ (30 ml). 1-Chlorocarbonyl-1-methylethylacetate (1.8 ml, 0.013 mol) was added and stirred for 3 hours at ambient temperature. Sat. aqueous solution of NaHCO$_3$ (20 ml) was added and extracted three times with ethyl acetate (50 ml). The organic layer was evaporated and dissolved in THF (50 ml). Sodium methoxide (0.53 g, 0.01 mol) was added and stirred for 6 hours. Sat. aqueous solution of NaHCO$_3$ (50 ml) was added and extracted with ethyl acetate (50 ml). The organic layer was dried over anhydrous MgSO$_4$ and evaporated to dryness. The crude product was purified by column chromatography on silica gel to give (S)-2,3-epoxy-1-propylcarbamate benzyl ester (90%, optical purity>99%ee).

$^1$H-NMR (CDCl$_3$, ppm): δ7.37 (s, 5H, Ph), 5.13 (s, 2H, CH$_2$—Ph), 4.98 (brs, 1H, NH), 3.66 (m, 1H, CH—O), 3.33–3.13 (m, 2H, CH$_2$—O), 2.81–2.60 (m, 2H, CH$_2$N)

EXAMPLE 11

Preparation of (S)-2,3-Dihydroxy-1-Propylamine Hydrochloric Acid Salt

NaOH (75 g) was dissolved in water (600 ml) in 500 ml three-necked flask equipped with thermometer and bromine (40 ml) was added with keeping temperature at 0° C. (S)3,4-Dihydroxy-1-butylamide (36.17 g, 0.301 mol) was added and stirred for 1 hour for 50° C. To aqueous solution distilled from reaction mixture was added 1N HCl. The reaction mixture was heated for 1 hour, distilled out water and dried to give white solid, (S)-2,3-dihydroxy-1-propyl amine hydrochloric acid salt (33.72 g, 87%, optical purity>99%ee).

$^1$H-NMR (D$_2$O, ppm) : δ3.82 (m, 1H, —CHOH), 3.52 (m, 2H, CH$_2$OH), 3.08–2.81 (m, 2H, CH$_2$N)

EXAMPLE 12

Preparation of (S)-2,3-Dihydroxy-1-Propylcarbamate Methyl Ester (S)-3,4-Dihydroxy-1-butylamide (22.2 g, 0.1 mol) in 500 ml flask equipped with thermometer was dissolved in methanol (90 ml). To the reaction mixture was added a solution of metallic Na (4.6 g, 0.2 mol) in methanol (145 ml). Bromine (16 g, 0.1 mol) was added and refluxed for 10 min. The reaction mixture was evaporated, dissolved in ethyl acetate and washed with water to remove sodium bromide. The organic layer was evaporated and dried. The crude product was purified by recrystallization from ethanol to give (S)-2,3-dihydroxy-1-propylcarbamate methyl ester (13.6 g, 91%, optical purity>99%ee).

$^1$H-NMR (D$_2$O, ppm): δ5.21 (brs, 1H, NH), 3.79 (m, 1H, —CHOH), 3.60 (m, 2H, CH$_2$OH), 3.65 (s, 3H, OCH$_3$), 3.60 (m, 2H, CH$_2$N)

As explained above, the process of this invention provides chiral (S)-2,3-disubstituted-1-propylamine derivatives with high optical purity and high yield by Curtius Rearrangement or Hofmann Rearrangement that may not influence on chiral hydroxyl group but decreases the number of carbon backbone. In addition, chiral (S)-3,4-disubstituted-1-butanecarbonyl derivatives used as starting material may be easily obtained from natural product or prepared by simple and inexpensive method, thereby decreasing the production cost.

What is claimed is:

1. A process for preparing chiral (S)-2,3-disubstituted-1-propylamine derivatives expressed in the following formula 1, characterized in that a carbonyl group of chiral (S)-3,4-disubstituted-1-butanecarbonyl derivatives expressed in the following formula 2 is converted to an amine group:

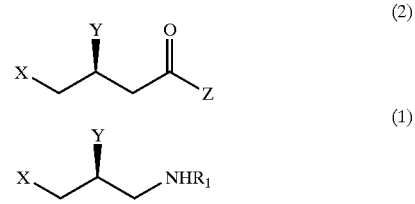

wherein,
  R$_1$ represents hydrochloric acid salt (H—HCl), sulfuric acid salt (H—H$_2$SO$_4$) or —C(O)OR$_2$;
  R$_2$ represents linear or branched alkyl chain having carbon atoms of 1–10, benzyl or phenyl group;
  X and Y which are same or different, represents a halogen atom, hydroxy group, acetate group, sulfonate group, or in which X and Y are combined to form epoxy group, acetonide group; and
  Z represents NH$_2$, NHNH$_2$ or hydroxy group.

2. The process for preparing chiral (S)-2,3-disubstituted-1-propylamine derivatives according to claim 1, wherein the conversion reaction is performed through Curtius Rearrangement or Hofmann Rearrangement.

3. The process for preparing chiral (S)-2,3-disubstituted-1-propylamine derivatives according to claim 1, wherein the carbonyl group of chiral (S)-3,4-disubstituted-1-butanecarbonyl derivatives expressed in the formula 2, in which Z is NHNH$_2$, is converted to amine group through Curtius Rearrangement.

4. The process for preparing chiral (S)-2,3-disubstituted-1-propylamine derivatives according to claim 3, wherein the Curtius Rearrangement employs metallic nitrite or alkylnitrite of C$_1$–C$_{10}$.

5. The process for preparing chiral (S)-2,3-disubstituted-1-propylamine derivatives according to claim 4, wherein the metallic nitrite is sodium nitrite or potassium nitrite.

6. The process for preparing chiral (S)-2,3-disubstituted-1-propylamine derivatives according to claim 4, wherein the metallic nitrite or alkylnitrite of $C_1$–$C_{10}$ is added at temperature in the range of −78–50° C.

7. The process for preparing chiral (S)-2,3-disubstituted-1-propylamine derivatives according to claim 4, wherein a reaction mixture is subjected to reflux following the addition of metallic nitrite or alkylnitrite of $C_1$–$C_{10}$.

8. The process for preparing chiral (S)-2,3-disubstituted-1-propylamine derivatives according to claim 7, wherein a solvent for reflux is aromatic hydrocarbon.

9. The process for preparing chiral (S)-2,3-disubstituted-1-propylamine derivatives according to claim 1, wherein the carbonyl group of chiral (S)-3,4-disubstituted-1-butanecarbonyl derivatives expressed in the formula 2, in which Z is —OH, is converted to amine group through Curtius Rearrangement.

10. The process for preparing chiral (S)-2,3-disubstituted-1-propylamine derivatives according to claim 9, wherein Curtius Rearrangement is performed in such a manner that haloformate or phosphoryl halide is added to the compound expressed in formula 2 (where, Z is —OH) and alkaline metal azide is subsequently added.

11. The process for preparing chiral (S)-2,3-disubstituted-1-propylamine derivatives according to claim 10, wherein the haloformate is a compound of the following formula 7 and the phosphoryl halide is a compound of the following formula 8:

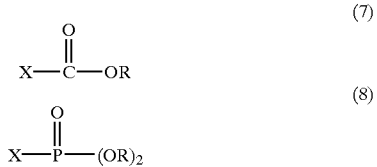

wherein,

X is halogen atom; and

R is alkyl group of $C_1$–$C_5$, benzyl, or phenyl group.

12. The process for preparing chiral (S)-2,3-disubstituted-1-propylamine derivatives according to claim 10 or 11, wherein the addition reaction is performed at temperature in the range of −78–50° C.

13. The process for preparing chiral (S)-2,3-disubstituted-1-propylamine derivatives according to claim 10, wherein the alkaline metal azide is sodium azide or potassium azide.

14. The process for preparing chiral (S)-2,3-disubstituted-1-propylamine derivatives according to claim 10 or 13, wherein a reaction temperature is maintained in the range of 50–150° C. following the addition of alkaline metal azide.

15. The process for preparing chiral (S)-2,3-disubstituted-1-propylamine derivatives according to claim 9, wherein a solvent for Curtius Rearrangement is aromatic hydrocarbon.

16. The process for preparing chiral (S)-2,3-disubstituted-1-propylamine derivatives according to claim 1, wherein the carbonyl group of chiral (S)-3,4-disubstituted-1-butanecarbonyl derivatives expressed in the formula 2, in which Z is —$NH_2$, is converted to amine group through Hofmann Rearrangement.

17. The process for preparing chiral (S)-2,3-disubstituted-1-propylamine derivatives according to claim 16, wherein the Hofmann Rearrangement is performed in the presence of alkaline metal hydroxide and halogen, or MOX (where, M is alkaline metal atom and X is halogen atom).

18. The process for preparing chiral (S)-2,3-disubstituted-1-propylamine derivatives according to claim 16 or 17, wherein a solvent for the Hofmann Rearrangement is water or polar organic solvent.

19. The process for preparing chiral (S)-2,3-disubstituted-1-propylamine derivatives according to claim 18, wherein the polar organic solvent is alcohol of $C_1$–$C_{10}$.

20. The process for preparing chiral (S)-2,3-disubstituted-1-propylamine derivatives according to claim 16, wherein the Hofmann Rearrangement is performed at temperature in the range of 0–100° C.

21. The process for preparing chiral (S)-2,3-disubstituted-1-propylamine derivatives according to claim 16, wherein the Hofmann Rearrangement is performed at temperature in the range of 0–60° C.

* * * * *